(12) United States Patent
Orr et al.

(10) Patent No.: US 9,889,080 B2
(45) Date of Patent: Feb. 13, 2018

(54) COLOR DEPOSITING SHAMPOO

(71) Applicant: Celeb LLC, Davie, FL (US)

(72) Inventors: Cindy Orr, Fort Lauderdale, FL (US); Lauren LaBeaud, Fort Lauderdale, FL (US); Leland Hirsch, Fort Lauderdale, FL (US)

(73) Assignee: Celeb LLC, Davie, FL (US)

( * ) Notice: Subject to any disclaimer, the term of this patent is extended or adjusted under 35 U.S.C. 154(b) by 7 days.

(21) Appl. No.: 15/140,064

(22) Filed: Apr. 27, 2016

(65) Prior Publication Data

US 2016/0324743 A1 Nov. 10, 2016

Related U.S. Application Data

(60) Provisional application No. 62/158,296, filed on May 7, 2015.

(51) Int. Cl.
*A61Q 5/10* (2006.01)
*A61K 8/42* (2006.01)
(Continued)

(52) U.S. Cl.
CPC ............... *A61K 8/42* (2013.01); *A61Q 5/02* (2013.01); *A61Q 5/065* (2013.01); *A61K 2800/432* (2013.01)

(58) Field of Classification Search
CPC .... A61K 8/42; A61K 2800/432; A61Q 5/065; A61Q 5/02
See application file for complete search history.

(56) References Cited

U.S. PATENT DOCUMENTS 2,338,746 A 1/1944 Van Riper
3,706,725 A 12/1972 Ozutsumi et al.
(Continued)

FOREIGN PATENT DOCUMENTS

CN 1291468 A 4/2001
CN 101305968 A 11/2008
(Continued)

OTHER PUBLICATIONS

International Search Report dated Aug. 11, 2016 from PCT/US16/31232.
(Continued)

*Primary Examiner* — Elisa B Elhilo
(74) *Attorney, Agent, or Firm* — Brad M. Behar & Associates, PLLC

(57) ABSTRACT

A composition for coloring and shampooing hair substantially free, preferably totally and completely free, of anionic surfactants, comprising at least one cationic dye, n-methyl alkyl glucamide with a carbon chain length from 8 and 20, inclusive, preferably 8 and 10, an aqueous carrier, and at least one stabilizer of anti-oxidant and free radical scavanger. By weight, (based on the total weight of the composition), the composition comprises 0.0005% to 3.0% cationic dye, 2.5 to 30% n-methyl alkyl glucamide, 30 to 70% water, and 0.01 to 0.5% stabilizers of anti-oxidant and free radical scavenger. Other ingredients, including a rheology modifying polymer, conditioning ingredients, and additional surfactants, may also be included in the composition and are also included in the scope of the invention.

28 Claims, 10 Drawing Sheets
(2 of 10 Drawing Sheet(s) Filed in Color)

APPLICANT'S EXAMPLE 1

| Ingredient INCI | Wt % |
|---|---|
| Water | 62.3800 |
| Guar Hydroxypropyltrimonium Chloride | 0.2000 |
| Polyacrylate-1 Crosspolymer | 3.0000 |
| n-methyl alkyl glucamide with a C-chain length of C8/C10 | 2.5000 |
| Lauramidopropyl Betaine | 9.0000 |
| Sodium Cocoamphoacetate | 9.0000 |
| Trisodium Ethylenediamine Disuccinate | 0.0500 |
| Sodium Benzoate | 0.5000 |
| Potassium Sorbate | 0.2000 |
| DL-Panthenol | 0.1000 |
| Hydrolyzed Pea Protein | 0.0100 |
| Tocopherol | 0.2000 |
| Sodium Citrate | 0.2000 |
| Fragrance | 0.5000 |
| Phytantriol | 0.1000 |
| Citric Acid | 1.6000 |
| Water | 10.0000 |
| Basic Brown 17 | 0.1300 |
| Basic Blue 99 | 0.1300 |
| Basic Red 76 | 0.2000 |
| | 100.0000 |

(51) Int. Cl.
*A61Q 5/02* (2006.01)
*A61Q 5/06* (2006.01)

(56) References Cited

U.S. PATENT DOCUMENTS

| | | | |
|---|---|---|---|
| 3,822,247 A | 7/1974 | Ozutsumi et al. |
| 3,920,384 A | 11/1975 | Feinland et al. |
| 4,172,703 A | 10/1979 | Fakhouri |
| 4,630,080 A | 12/1986 | Satake et al. |
| 4,662,892 A | 5/1987 | Pike |
| 4,875,902 A | 10/1989 | Grollier et al. |
| 4,900,468 A | 2/1990 | Mitchell et al. |
| 5,032,138 A | 7/1991 | Wolfram et al. |
| 5,067,966 A | 11/1991 | Mager et al. |
| 5,085,857 A | 2/1992 | Reid et al. |
| 5,507,063 A | 4/1996 | Hirsch |
| 5,520,707 A | 5/1996 | Lim et al. |
| 5,637,115 A | 6/1997 | Balzer et al. |
| 5,643,341 A | 7/1997 | Hirsch et al. |
| 5,733,536 A | 3/1998 | Hill et al. |
| 5,855,626 A | 1/1999 | Wiegner et al. |
| 5,891,200 A | 4/1999 | Lim et al. |
| 5,922,310 A | 7/1999 | Chaudhuri et al. |
| 5,961,664 A | 10/1999 | Anderson |
| 5,981,548 A | 11/1999 | Paolini et al. |
| 5,997,764 A | 12/1999 | Ambuter et al. |
| 6,008,359 A | 12/1999 | Jachowicz et al. |
| 6,083,422 A | 7/2000 | Ambuter et al. |
| 6,231,877 B1 | 5/2001 | Vacher et al. |
| 6,395,258 B1 | 5/2002 | Steer |
| 6,440,177 B1 | 8/2002 | Orr |
| 6,475,248 B2 | 11/2002 | Ohashi et al. |
| 6,500,413 B1 | 12/2002 | Kapsner et al. |
| 6,530,959 B1 | 3/2003 | Lang et al. |
| 6,592,632 B2 | 7/2003 | Vainshelboim et al. |
| 6,616,708 B2 | 9/2003 | Ohashi et al. |
| 6,635,262 B2 | 10/2003 | Jourdan et al. |
| 6,699,463 B2 | 3/2004 | Chaudhuri |
| 6,746,493 B2 | 6/2004 | Miyabe et al. |
| 6,814,762 B2 | 11/2004 | Matsunaga |
| 6,878,169 B2 | 4/2005 | Matsunaga |
| 7,012,048 B2 | 3/2006 | Drovetskaya et al. |
| 7,048,770 B2 | 5/2006 | Azizova et al. |
| 7,056,355 B2 | 6/2006 | Pratt et al. |
| 7,087,221 B2 | 8/2006 | Royce et al. |
| 7,135,168 B2 | 11/2006 | Miczewski et al. |
| 7,172,632 B2 | 2/2007 | Smith et al. |
| 7,217,752 B2 | 5/2007 | Schmucker-Castner et al. |
| 7,378,479 B2 | 5/2008 | Tamareselvy et al. |
| 7,494,514 B2 | 2/2009 | Narasimhan et al. |
| 7,527,653 B2 | 5/2009 | Azizova et al. |
| 7,528,100 B2 | 5/2009 | Gunn et al. |
| 7,578,857 B1* | 8/2009 | Massoni ............... A61K 8/40 132/202 |
| 7,604,796 B2 | 10/2009 | Watanabe |
| 7,651,538 B2 | 1/2010 | Yamaguchi et al. |
| 7,699,897 B2 | 4/2010 | Nguyen et al. |
| 7,736,396 B2 | 6/2010 | Fukuhara et al. |
| 7,749,284 B2 | 7/2010 | Lockridge et al. |
| 7,758,659 B2 | 7/2010 | Massoni |
| 7,824,449 B2 | 11/2010 | Hayama et al. |
| 7,857,862 B2 | 12/2010 | Koike et al. |
| 7,857,863 B2 | 12/2010 | Koike et al. |
| 7,862,625 B2 | 1/2011 | Koike et al. |
| 7,985,266 B2 | 7/2011 | Zhang et al. |
| 8,118,881 B2 | 2/2012 | Yamaguchi et al. |
| 8,207,108 B2 | 6/2012 | Jermann et al. |
| 8,227,426 B2 | 7/2012 | Gupta et al. |
| 8,298,298 B1 | 10/2012 | Miller |
| 8,313,537 B2 | 11/2012 | Xue et al. |
| 8,318,143 B2 | 11/2012 | Van Gogh et al. |
| 8,343,469 B2 | 1/2013 | Bierganns et al. |
| 8,357,356 B2 | 1/2013 | Zaeska et al. |
| 8,361,167 B2 | 1/2013 | Blackburn et al. |
| 8,394,361 B1 | 3/2013 | Frantz et al. |
| 8,394,851 B2 | 3/2013 | Gupta et al. |
| 8,440,174 B2 | 5/2013 | Panandiker et al. |
| 8,450,294 B2 | 5/2013 | Lepilleur et al. |
| 8,529,637 B2 | 9/2013 | Vohra et al. |
| 8,541,352 B2 | 9/2013 | Randall et al. |
| 8,637,569 B2 | 1/2014 | Birbara |
| 8,663,340 B2 | 3/2014 | Sutton et al. |
| 8,673,371 B2 | 3/2014 | Kim et al. |
| 8,702,814 B2 | 4/2014 | Sutton et al. |
| 8,709,100 B2 | 4/2014 | Sutton et al. |
| 8,735,533 B2 | 5/2014 | Hong et al. |
| 8,795,644 B2 | 8/2014 | Tan et al. |
| 8,795,646 B2 | 8/2014 | Coore |
| 8,802,069 B2 | 8/2014 | Tan et al. |
| 8,802,070 B2 | 8/2014 | Tan et al. |
| 8,829,118 B2 | 9/2014 | Hessefort et al. |
| 8,939,158 B2 | 1/2015 | Mercier et al. |
| 9,096,882 B2 | 8/2015 | Meyer et al. |
| 2002/0015718 A1 | 2/2002 | Kruse et al. |
| 2002/0042958 A1 | 4/2002 | Orr et al. |
| 2002/0046430 A1 | 4/2002 | Matsunaga et al. |
| 2003/0198607 A1 | 10/2003 | Chaudhuri |
| 2004/0040095 A1 | 3/2004 | King et al. |
| 2005/0011012 A1 | 1/2005 | Sun et al. |
| 2005/0112074 A1 | 5/2005 | Arai et al. |
| 2006/0070191 A1 | 4/2006 | Lang |
| 2006/0269501 A1 | 11/2006 | Johnson et al. |
| 2007/0017039 A1 | 1/2007 | Errey et al. |
| 2007/0251029 A1 | 11/2007 | Bureiko et al. |
| 2007/0269466 A1 | 11/2007 | Wakefield et al. |
| 2009/0068278 A1 | 3/2009 | Golz-Berner et al. |
| 2009/0214459 A1 | 8/2009 | Ascione et al. |
| 2009/0320215 A1 | 12/2009 | Massoni |
| 2010/0064449 A1 | 3/2010 | Khan et al. |
| 2010/0125956 A1 | 5/2010 | Koike et al. |
| 2010/0143274 A1 | 6/2010 | Deshayes et al. |
| 2010/0158830 A1 | 6/2010 | Wei et al. |
| 2010/0197812 A1 | 8/2010 | Nahas et al. |
| 2011/0035885 A1 | 2/2011 | Zhang et al. |
| 2011/0035886 A1 | 2/2011 | Zhang et al. |
| 2011/0236324 A1 | 9/2011 | Deo |
| 2012/0171156 A1 | 7/2012 | Basketter et al. |
| 2012/0230925 A1 | 9/2012 | Wagner et al. |
| 2012/0230968 A1 | 9/2012 | Worden, Sr. |
| 2012/0276210 A1 | 11/2012 | Dihora et al. |
| 2013/0101515 A1 | 4/2013 | Meyer et al. |
| 2014/0026332 A1 | 1/2014 | Jo et al. |
| 2014/0044762 A1 | 2/2014 | Colaco et al. |
| 2014/0193350 A1 | 7/2014 | Bauer et al. |
| 2014/0227328 A1 | 8/2014 | Dihora et al. |
| 2014/0242018 A1* | 8/2014 | Zasloff ............... A61K 47/26 424/70.31 |
| 2014/0287973 A1 | 9/2014 | Sivik et al. |
| 2014/0329428 A1 | 11/2014 | Glenn, Jr. et al. |

FOREIGN PATENT DOCUMENTS

| | | |
|---|---|---|
| CN | 101357106 A | 2/2009 |
| CN | 103932967 A | 7/2014 |
| CN | 103360789 B | 4/2015 |
| EP | 0137178 A2 | 4/1985 |
| EP | 0503507 A1 | 9/1992 |
| EP | 0559376 A1 | 9/1993 |
| EP | 1153598 A2 | 11/2001 |
| EP | 1369105 A1 | 12/2003 |
| EP | 1484048 A1 | 12/2004 |
| EP | 1915984 A1 | 4/2008 |
| EP | 1535599 B1 | 1/2013 |
| WO | WO 199417783 | 8/1994 |
| WO | WO 2002042380 A1 | 5/2002 |
| WO | WO 2002051370 A1 | 7/2002 |
| WO | WO 2004087086 A2 | 10/2004 |
| WO | WO 2008003529 A1 | 1/2008 |

(56) References Cited

FOREIGN PATENT DOCUMENTS

| WO | WO 2008020730 A1 | 2/2008 |
|----|------------------|--------|
| WO | WO 2014029843 A1 | 2/2014 |

OTHER PUBLICATIONS

Third Party Observations for international counterpart application No. PCT/US2016/031232 dated Jul. 20, 2017.

\* cited by examiner

APPLICANT'S EXAMPLE 1

| Ingredient INCI | Wt % |
| --- | --- |
| Water | 62.3800 |
| Guar Hydroxypropyltrimonium Chloride | 0.2000 |
| Polyacrylate-1 Crosspolymer | 3.0000 |
| n-methyl alkyl glucamide with a C-chain length of C8/C10 | 2.5000 |
| Lauramidopropyl Betaine | 9.0000 |
| Sodium Cocoamphoacetate | 9.0000 |
| Trisodium Ethylenediamine Disuccinate | 0.0500 |
| Sodium Benzoate | 0.5000 |
| Potassium Sorbate | 0.2000 |
| DL-Panthenol | 0.1000 |
| Hydrolyzed Pea Protein | 0.0100 |
| Tocopherol | 0.2000 |
| Sodium Citrate | 0.2000 |
| Fragrance | 0.5000 |
| Phytantriol | 0.1000 |
| Citric Acid | 1.6000 |
| Water | 10.0000 |
| Basic Brown 17 | 0.1300 |
| Basic Blue 99 | 0.1300 |
| Basic Red 76 | 0.2000 |
|  | 100.0000 |

Figure 1

| FORMULA | FOAM HEIGHT (CM) | NOTES |
|---|---|---|
| Example 1 | 2.875 | Amphoteric, nonionic base with glucamide |
| Comparative Example A | 3.334 | Anionic, sulfate base |
| Comparative Example B | 1.905 | Anionic, citrate base |
| Comparative Example C | 1.905 | Anionic, sarcosinate base |
| Comparative Example D | 1.746 | Amphoteric, nonionic base |

Figure 7

COMPARATIVE EXAMPLE A

| Ingredient INCI | Wt % |
|---|---|
| Water | 45.6400 |
| Polyacrylate-1 Crosspolymer | 5.0000 |
| Sodium Laureth Sulfate | 20.0000 |
| Coco-Glucoside (and) Glyceryl Oleate | 3.0000 |
| Water (and) Laurylamidopropyl Betaine' | 5.5000 |
| Water (and) Ammonium Laureth Sulfate | 15.0000 |
| Glycol Distearate (and) Laureth-4 (and) Cocamidopropyl Betaine | 3.0000 |
| Tocopherol | 0.1000 |
| Water (and) Sodium Benzoate (and) Potassium Sorbate | 0.7000 |
| Sodium Cocoyl Hydrolyzed Wheat Protein | 0.5000 |
| Fragrance | 0.1000 |
| Water (and) Citric Acid | 1.0000 |
| Basic Brown 17 | 0.1300 |
| Basic Blue 99 | 0.1300 |
| Basic Red 76 | 0.2000 |
|  | 100.0000 |

Figure 8

COMPARATIVE EXAMPLE B

| Ingredient INCI | Wt % |
|---|---|
| Water | 75.640 |
| Disodium Cocoamphoacetate | 0.750 |
| Cocamidopropylamine Betaine | 10.000 |
| Cocamidopropylamine Oxide | 6.000 |
| Disodium Cocopolyglucose Citrate | 6.200 |
| PEG-120 Methyl Glucose Dioleate | 0.750 |
| Lauramide MEA | 0.100 |
| Dimethicone Copolyol Laurate | 0.100 |
| Basic Brown 17 | 0.130 |
| Basic Blue 99 | 0.130 |
| Basic Red 76 | 0.200 |
| | 100.000 |

Figure 9

COMPARATIVE EXAMPLE C

| Ingredient INCI | Wt % |
|---|---|
| Water | 58.190 |
| Guar Hydroxypropyltrimonium Chloride | 0.750 |
| Sodium Lauroyl Sarcosinate | 10.000 |
| Lauramidopropyl Betaine | 10.000 |
| Cocamidopropylamine Oxide | 6.000 |
| Lauramide MEA | 6.200 |
| Hydroxyethylcellulose | 0.750 |
| Disodium EDTA | 0.100 |
| Sodium Citrate | 0.100 |
| Caramel | 0.700 |
| Basic Brown 17 | 0.130 |
| Basic Blue 99 | 0.130 |
| Basic Red 76 | 0.200 |
| Mica/Titanium Dioxide | 3.000 |
| Preservative | 1.000 |
| Fragrance | 0.750 |
| Quaternium 91 (and)Cetrimonium Methosulfate (and) Cetearyl Alcohol | 2.000 |
| | 100.000 |

Figure 10

COMPARATIVE EXAMPLE D

| Ingredient INCI | Wt % |
|---|---:|
| Water | 64.4900 |
| Acrylates Crosspolymer-4 | 10.0000 |
| Disodium EDTA | 0.0500 |
| Butylene Glycol | 5.0000 |
| Sodium Cocoamphoacetate | 11.1000 |
| Cocamidopropyl Betaine | 3.0000 |
| Polyquaternium-39 | 0.8000 |
| Preservative | 0.4500 |
| Sodium Hydroxide | 0.2500 |
| Basic Brown 17 | 0.1300 |
| Basic Blue 99 | 0.1300 |
| Basic Red 76 | 0.2000 |
| PEG-12 Dimethicone | 0.2000 |
| Decyl Glucoside | 4 |
| Mica | 0.2 |
| | 100.0000 |

Figure 11

APPLICANT'S EXAMPLE 2

| Ingredient INCI | Wt % |
|---|---|
| Water | 52.4910 |
| Guar Hydroxypropyltrimonium Chloride | 0.2000 |
| Polyacrylate-1 Crosspolymer | 3.0000 |
| Capryloyl/Caproyl Glucamide | 30.000 |
| Lauramidopropyl Betaine | 1.0000 |
| Sodium Cocoamphoacetate | 0.0000 |
| Trisodium Ethylenediamine Disuccinate | 0.0500 |
| Sodium Benzoate | 0.5000 |
| Potassium Sorbate | 0.2000 |
| Fragrance | 0.5000 |
| Phytantriol | 0.1000 |
| Citric Acid | 1.6000 |
| Water | 10.0000 |
| Basic Brown 17 | 0.2000 |
| HC Blue 16 | 0.0300 |
| Basic Yellow 87 | 0.1000 |
| Basic Red 51 | 0.0070 |
| Basic Orange 31 | 0.0220 |
| | 100.0000 |

Figure 12

COLOR DEPOSITING SHAMPOO

FIELD OF THE INVENTION

The present invention relates to compositions for coloring and cleansing hair using a one-part formulation. More specifically, the invention relates to shampoo compositions containing at least one cationic dye and a nonionic surfactant with improved foaming ability compared to existing color depositing shampoo products.

BACKGROUND

Basic cationic hair dyes have been available for use in cosmetic products for more than twenty years. They have been adapted for use in color refreshing shampoo and conditioners, temporary hair color gels, and cremes. The products are intended to enhance and refresh previously colored hair, neutralize an unwanted shade, bring new highlights, and create visible color change.

One of the main drawbacks for cationic dyes in many types of hair care products is they are not useful in combination with or within products containing anionic ingredients, particularly anionic surfactants. The combination of cationic dyes and anionic ingredient(s) in a single product, e.g., a color depositing shampoo, causes a reduction of foaming properties (in a shampoo, foaming is recognized as being a desirable attribute. A shampoo that does not foam or does not foam adequately or with a suitable foam quality generally has perceived consumer negatives) and reduced color deposition. The combination of the two could also cause precipitation of an unwanted anionic/cationic complex. Common industry practice therefore utilizes high levels/quantities of cationic dyes in order to compensate for these drawbacks while still achieving a desired level of color deposition. Consequently, existing color depositing shampoos must use greater amounts of dye in the products to account for the "waste" causing higher costs of goods and thus higher retail prices effectively rendering combined cationic dye with anionic surfactant products highly difficult to market.

The current industry alternative for color depositing shampoos is a combination of a cationic dye with amphoteric and/or nonionic surfactants. Those products do not suffer from the above stated disadvantages arising primarily from the opposing ionic charges of the dye and surfactant. Here again, however, there are well known disadvantages. One problem with coloring shampoos which are generally free of anionic surfactants (that is, they are based on nonionic, amphoteric and/or cationic surfactants) is that they have a tendency not to foam adequately or may have poor sensory properties associated with the foaming, such as a tendency for any foam that does generate to generate slowly, spread slowly, or to dissipate quickly. The viscosity of the product(s) is also difficult to control. Addition of a small amount of an anionic surfactant (which adds to the production steps and increases cost of goods) is sometimes done to improve the foaming properties of a dye product made with a nonionic, amphoteric and/or cationic surfactants, knowing the resulting product will suffer from decreased dye deposition and/or suffer long term stability issues such as tonal shifts, precipitation or separation.

Thus there is a need for a color depositing shampoo made with cationic dyes that is substantially free from anionic surfactants with good foaming properties to efficiently and effectively deliver the dyes to the hair. It would be highly beneficial to have a color depositing shampoo that can achieve equal, if not more, dye deposition (and thus color change) compared to existing products, using less dye within the compositions of those existing products. There is a need for a color depositing shampoo that has less waste of dye when used. There is a need for a lower cost to manufacture color depositing shampoo that can effectively deposit color with good foaming properties.

It is thus an object of the present invention to provide a shampoo based formulation that will efficiently color the hair and effectively clean the hair. It is also an object of the invention to provide a shampoo based formulation that will replace ordinary shampoo but also be useful as a hair dye, a composition with improved and more desirable foaming properties.

SUMMARY OF THE INVENTION

Applicant has invented a composition that overcomes these and other shortcomings. While the invention will be described in connection with certain embodiments, it will be understood that the invention is not limited to those embodiments. To the contrary, the invention includes all alternatives, modifications and equivalents as may be included within the spirit and scope of the present invention.

Applicant has surprisingly discovered that the combination of a specific non-ionic surfactant, namely n-methyl alkyl glucamide, with a cationic dye(s) can be used to create an effective and efficient color depositing shampoo with unexpected and desirable foaming properties. Thus, Applicant has discovered that a color depositing shampoo with preferred foaming properties can be made without the need for extra dye and without any anionic surfactant. Applicant has discovered an efficient, effective, lower dye composition, color depositing shampoo with desirable foaming properties comprising a cationic dye and n-methyl alkyl glucamide. Applicant has discovered that use of n-methyl alkyl glucamide with a chain length anywhere from 8 to 20 is possible and included within the scope of the invention, with a $C_8/C_{10}$ carbon chain length most preferred for its lathering properties. The invention allows for efficient dye deposition with commercially acceptable foaming characteristics. The composition of the present invention thus provides unexpected superior results for a shampoo capable of depositing color with desirable foaming The present invention relates to the application of cationic dyes to human hair using a one-part shampoo based formulation. The invention is a cleansing and coloring composition that is substantially free, preferably totally and completely free, of anionic surfactants. In one embodiment, said composition according to the invention comprises:
  (a) at least one cationic dye;
  (b) n-methyl alkyl glucamide with a carbon chain length between 8 and 20 ($C_8$-$C_{20}$), inclusive, preferably 8 ($C_8$) and 10 ($C_{10}$);
  (c) an aqueous carrier; and
  (d) at least one stabilizer of anti-oxidant and free radical scavenger.

Optionally, other ingredients that may be added to the composition but which are not necessary for the composition, include a rheology modifying polymer, conditioning ingredients, and additional surfactants.

The color depositing shampoo composition according to the invention comprises, by weight (all the weight percents are based on the total weight of the composition):
  (a) 0.0005% to 3.0% cationic dye;
  (b) 2.5 to 30% n-methyl alkyl glucamide;
  (c) 30 to 70% water; and
  (d) 0.01 to 0.5% stabilizers of anti-oxidant and free radical scavenger.

The properties of the invention are surprising and unique over existing technologies because the composition effectively delivers acceptable and efficient color to hair along with a consumer acceptable foam. The color and long term stability of the composition continues to deliver the same amount of color to the hair. Formulas with materials that are anionic deliver less color to the hair and overtime are seen to deliver less or undesirable results. The foaming characteristics of the invention is closer to the amount of foam delivered from a traditional anionic, sulfate shampoo.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the invention and, together with the general description of the invention given above and the detailed description of an embodiment given below, serve to explain the principles of the present invention. Similar components of the devices are similarly numbered for simplicity.

FIG. 1 illustrates the composition for one example embodiment of the invention with the percentages representing the amount by weight compared to total weight of the composition.

FIG. 7 contains a table showing the results of the foaming tests for the compositions tested.

FIGS. 8-11 contain tables with the compositions of the comparative examples tested and compared to test results for Applicant's example composition.

FIG. 12 illustrates the composition for a second example embodiment of the invention with the percentages representing the amount by weight compared to total weight of the composition.

DETAILED DESCRIPTION OF THE INVENTION

Reference is being made in detail to presently preferred embodiments of the invention. Selective embodiments are provided by way of explanation of the invention, which is not intended to be limited thereto. In fact, those of ordinary skill in the art may appreciate upon reading the present specification and viewing the present drawings that various modifications and variations can be made.

The present invention is a one-part shampoo based composition for cleansing and coloring hair that is substantially free, preferably totally and completely free, of anionic surfactants. In one embodiment, the composition according to the invention comprises:
  (a) at least one cationic dye;
  (b) n-methyl alkyl glucamide with a carbon chain length between 8 and 20, inclusive, preferably 8 and 10;
  (c) an aqueous carrier; and
  (d) at least one stabilizer of anti-oxidant and free radical scavenger.

Optionally, other ingredients that may be added to the composition but which are not necessary for the composition, include a rheology modifying polymer, conditioning ingredients, and additional surfactants.

The color depositing shampoo composition according to the invention comprises, by weight (all the weight percents are based on the total weight of the composition):
  (a) 0.0005% to 3.0% cationic dye;
  (b) 2.5 to 30% n-methyl alkyl glucamide;
  (c) 30 to 70% water; and
  (d) 0.01 to 0.5% stabilizers of anti-oxidant and free radical scavenger.

It being understood that the above described compositions are open to the inclusion of other ingredients that may alter the characteristics of the formula without rendering the system inoperative as a color depositing shampoo.

Use of a stabilizer prevents a shift in the color deposition as the product ages and is exposed to heat. The stabilizer consist of an anti-oxidant and free radical scavenger, such as, for example, tocopherol and sodium citrate.

Other active ingredients may include rheology modifiers, fragrances, chelating agents, opacifiers, conditioning ingredients and other adjuvants. Optionally, suitable amphoteric, nonionic and/or cationic surfactants may be added to the compositions of the invention as desired. Compositions of this invention may contain any other non-anionic ingredients normally used in hair shampoos. These other ingredients may include proteins, fragrances, preservatives, thickeners, conditioners, humectants, opacifiers, and/or pH adjustors.

Figure 2:
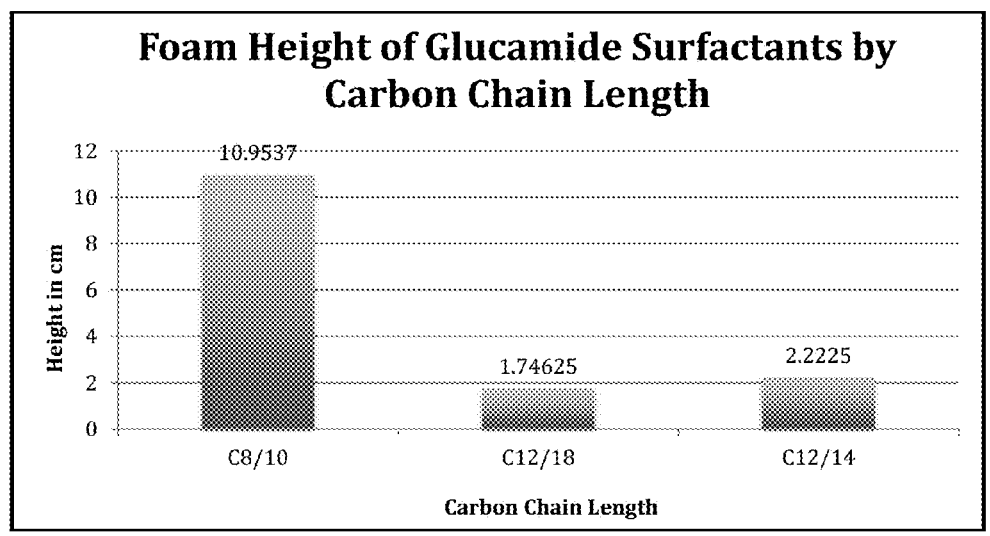
FIG. 2 is a graph showing the foaming properties of n-methyl alkyl glucamide surfactants having different carbon chain lengths.

FIG. 1 illustrates the composition for one example embodiment of the invention with the percentages representing the amount by weight compared to total weight of the composition. In FIG. 1, the n-methyl alkyl glucamide has a carbon chain length of eight and ten (C8/C10). Applicant has surprisingly discovered that using a n-methyl alkyl glucamide surfactant with a C8/C10 carbon chain length produces a non-ionic based surfactant shampoo with superior foaming properties when cationic dyes are incorporated to create a color depositing shampoo. As shown in FIG. 2, the foaming properties of a shampoo made from n-methyl alkyl glucamide is greatest when the carbon chain length is C8/C10, and decreases as the carbon chain length increases, such as seen in the results for the C12/C14 and the C12/C18 chain length ranges. The n-methyl alkyl glucamide surfactant used in the composition of an embodiment of the invention is not, however, limited to just the C8/C10 carbon chain length. The invention also includes embodiments comprising other carbon chain lengths of the n-methyl alkyl glucamide surfactant in the composition. For example, an embodiment may include a combination of n-methyl alkyl glucamide surfactant having carbon chain lengths C8 to C12, or C8 to C14, or C12 to C14, and others. Combinations of different carbon chain lengths ranging from $C_8$ to $C_{20}$ are possible and included in the scope of the invention. The n-methyl alkyl glucamide surfactant may be one from the group consisting of capryloyl/caproyl methyl glucamide, lauroyl/myristoyl methyl glucamide, and cocoyl methyl glucamide. The dye may be at least one from the group consisting of Basic Blue 124, Basic Yellow 87, Basic Red 51, Basic Orange 31, Basic Brown 17, Basic Blue 99, HC Blue 16, HC Blue 15, Basic Violet 2, Basic Brown 16, and Basic Yellow 57.

The compositions of the invention may be made by dispersing the ingredients in water followed by the application of sufficient heat to dissolve the ingredients without causing decomposition. For example, the procedure to create the example composition identified in FIG. 1 is as follows:

1. To vessel, add water and disperse guar hydroxypropyltrimonium chloride with a prop mixer.
2. Add polyacrylate-1 cross polymer with continued mixing.
3. Add surfactants, chelator, preservatives, panthenol and protein.
4. Premix the fragrance and the phytantriol and add to main batch.
5. Adjust pH to between 4.5 and 5.0 with citric acid. Continue mixing for 45 minutes.
6. In a separate vessel, charge water and add dyes. Heat to 60 degrees Celsius and mix until dyes are dissolved. Add to main vessel and mix until uniform.

The superior color depositing and foaming properties of the shampoo according to the invention is depicted by way of a comparison with existing compositions. Applicant's color depositing shampoo according to the example embodiment in FIG. 1 (an illustration of the invention and not intended to limit same) was compared to four other shampoos that impart color to the hair and those products are described in published patent references. For purposes of the comparison, Applicant's composition is identified as "Example 1" and the other compositions are identified as "A", "B", "C" and "D". The compositions were all produced exactly as disclosed in the patent references, and the dye colors were replaced with the same basic cationic dye colors used in Example 1 and in equal amounts, that is 0.13% basic brown 17, 0.13% basic blue 99, and 0.2% basic red 76, for a total dye composition of 0.46% by weight.

Example 1 and all four comparative compositions (A, B, C, and D) were evaluated by the same two tests, one to measure the amount of hair color change resulting from use (the amount of dye deposition), and one to measure foaming.

Figure 3:
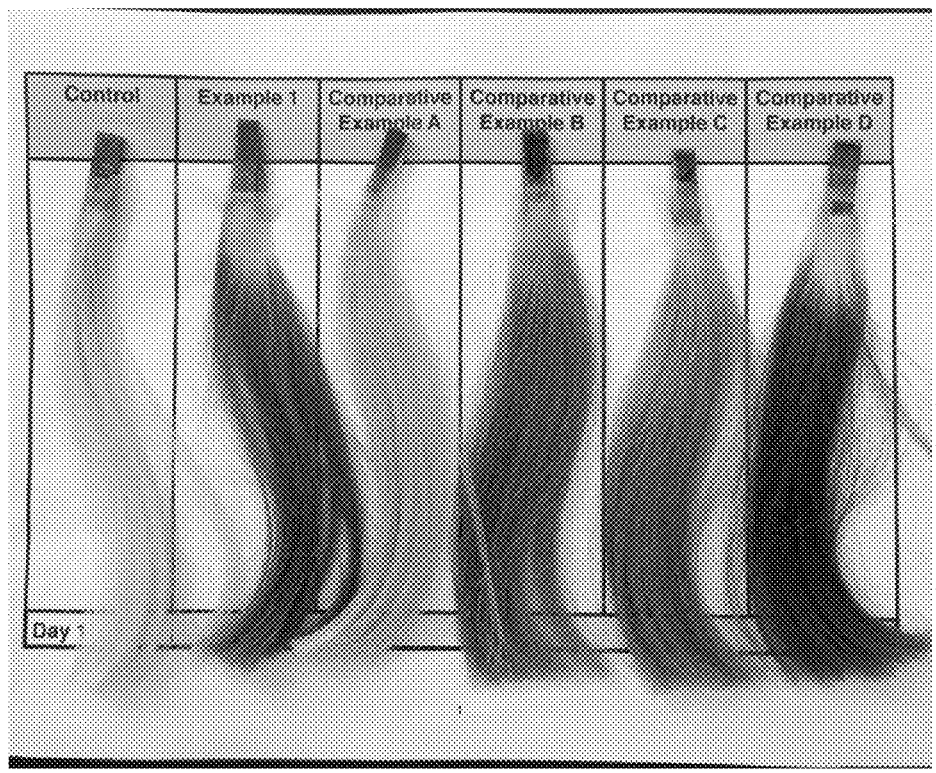
FIGS. 3 and 5 include pictures of swatches dyed with a composition according to the invention and four other comparative compositions at day 1 and day 21, respectively.
Figure 4:
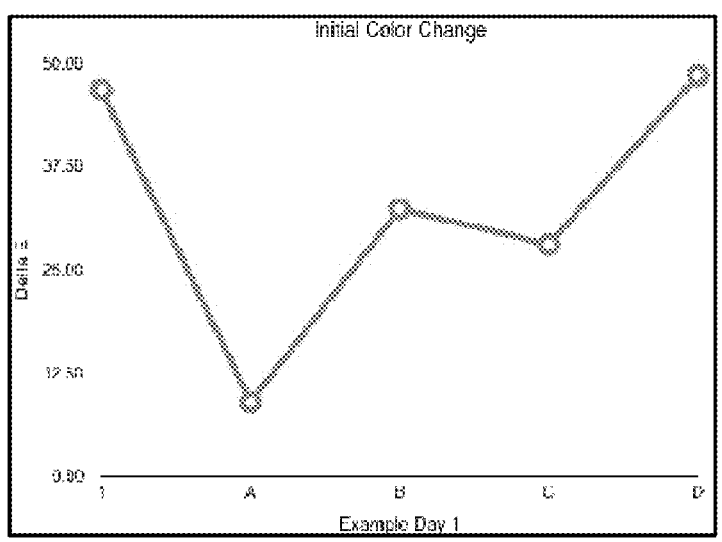
FIGS. 4 and 6 are line graphs showing the change in color for the swatches compared to the control bleached swatch (overall color change $\Delta E = SQRT(\Delta L^2 + \Delta a^2 + \Delta b^2)$) at day 1 and day 21, respectively.
Figure 5:
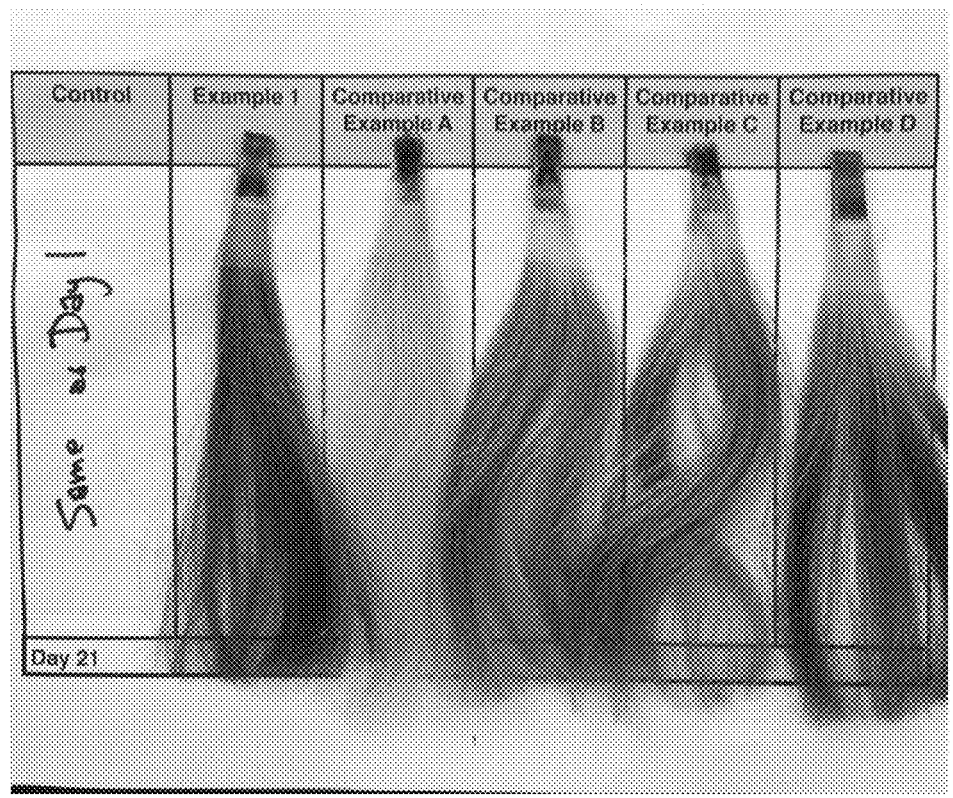
Figure 6:
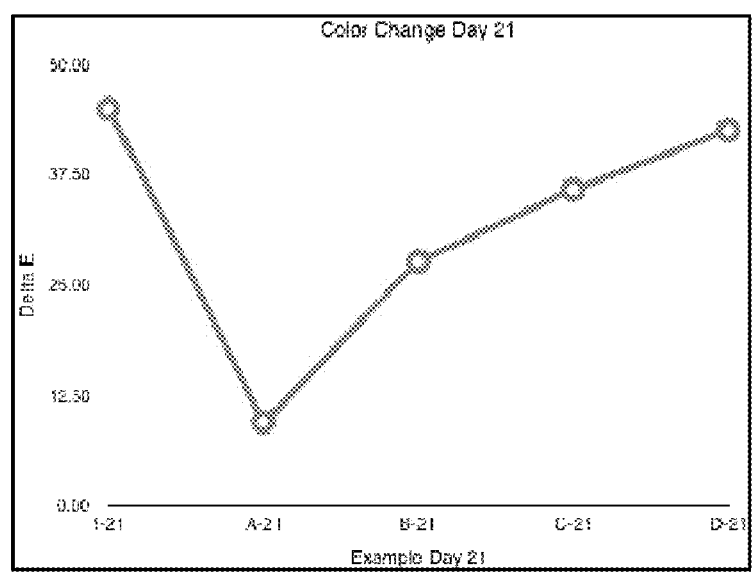

For the dye deposition measurement test, bleached hair swatches supplied by International Hair Importers were used. Each swatch was dyed out with one of the compositions, the dye out procedure involved one lather of the shampoo with rinsing, followed by blow drying of the swatch. The procedure was repeated after a 21 day period on new swatches. The color was visually assessed at day 1 and at day 21 with side by side comparisons of the swatches. The amount of color change was also measured at day 1 and day 21 on the CIELAB scale using a Hunter Lab Ultra Scan XE Colormeter. FIGS. 3 and 5 include pictures of the swatches at day 1 and day 21, respectively. FIGS. 4 and 6 are line graphs showing the overall color change (ΔE) for the swatches at day 1 and day 21, respectively.

The foaming of each shampoo was assessed by a blender test modified version of ASTM D3519-88 Foam in aqueous media (blender test). 1.0 grams of shampoo was mixed with 99.0 grams deionized water until homogeneous. The shampoo solution was put into a Bodum blender and run on "high" for 60 seconds. The height of the foam was measured. FIG. 7 contains a table showing the results of the foaming test.

Comparative example A is from Tamareselvy et. al. (U.S. Pat. No. 7,378,479), which discloses the combination of the cationic dyes with anionic surfactants (sodium and ammonium laureth sulfates), in combination with amphoteric surfactants (such as cocamidopropyl betaine) and cationic compatible amino-substituted vinyl polymer as a shampoo for color treatment and color maintenance. The composition for A produced and tested is set forth in FIG. 8. As shown in the results, significantly less color deposition occurred on the swatch for A compared to Applicant's Example 1.

Comparative example B is from Kapsner, et. al. (U.S. Pat. No. 6,500,413 B1) which discloses the combination of one or more cationic components in an anionic system provided the predominant anionic surfactant is an alkyl glucoester. The composition for B produced and tested is set forth in FIG. 9. As shown in the results, less color deposition occurred compared to Example 1 and B produced significantly less foaming compared to Example 1.

Comparative example C is from Massoni (U.S. Pat. No. 7,578,857 B1) which discloses use of cationic dyes, amphoteric surfactants, nonionic surfactants and an anionic sarcosinate surfactant for a shampoo coloring formulation. The composition for C produced and tested is set forth in FIG. 10. As shown in the results, less color deposition occurred compared to Example 1 and C produced significantly less foaming compared to Example 1.

Comparative example D is from Schmucker-Castner et. al., (U.S. Pat. No. 7,217,752) which discloses a stable, aqueous composition containing a substantially cross linked alkali-swellable acrylate copolymer rheology modifier, a surfactant, an alkaline material and various compounds requiring suspension or stabilization. Additionally, the reference discloses a phase stable cationic dye composition. The composition for D produced and tested is set forth in FIG. 11. Although the amount of color deposition compared to Example 1 may be close, D provides significantly less foaming than Example 1.

Accordingly, none of the other compositions tested provide the same or an equivalent ability to color hair and foam.

It should be understood, of course, that the foregoing relates to exemplary embodiments of the invention and that modifications may be made without departing from the spirit and scope of the present invention.

We claim:

1. A one-part coloring depositing shampoo composition for human hair comprising:
    at least one cationic dye;
    a non-ionic surfactant that is n-methyl alkyl glucamide with a carbon chain length of 8 and 10; and
    an aqueous carrier;
    wherein said composition does not contain any anionic surfactant.

2. The composition of claim 1, wherein the composition comprises, by weight:
    0.0005% to 3.0% cationic dye;
    2.5 to 30% n-methyl alkyl glucamide; and
    30 to 70% aqueous carrier.

3. The composition of claim 2, wherein said n-methyl alkyl glucamide is selected from the group consisting of capryloyl/caproyl methyl glucamide and cocoyl methyl glucamide.

4. The composition of claim 2, further comprising an amphoteric surfactant or a nonionic surfactant.

5. The composition of claim 2, further comprising a thickener.

6. The composition of claim 2, further comprising a stabilizer.

7. The composition of claim 2, further comprising an opacifier.

8. The composition of claim 2, further comprising a chelating agent.

9. The composition of claim 2, wherein said cationic dye is at least one from the group consisting of Basic Blue 124, Basic Yellow 87, Basic Red 51, Basic Orange 31, Basic Brown 17, Basic Blue 99, HC Blue 16, HC Blue 15, Basic Violet 2, Basic Brown 16, and Basic Yellow 57.

10. The composition of claim 2, wherein said aqueous carrier is water.

11. The composition of claim 1, wherein the composition comprises, by weight:
   less than 0.50% cationic dye;
   2.5 to 30% n-methyl alkyl glucamide; and
   30 to 70% water.

12. The composition of claim 11, wherein said cationic dye composition is about 0.46% by weight.

13. The composition of claim 12, wherein said n-methyl alkyl glucamide is about 2.5% by weight.

14. A method of dyeing human hair, which comprises shampooing the hair with the composition as claimed in claim 1.

15. A method of dyeing human hair, which comprises shampooing the hair with the composition as claimed in claim 2.

16. A method of dyeing human hair, which comprises shampooing the hair with the composition as claimed in claim 3.

17. A method of dyeing human hair, which comprises shampooing the hair with the composition as claimed in claim 4.

18. A method of dyeing human hair, which comprises shampooing the hair with the composition as claimed in claim 5.

19. A method of dyeing human hair, which comprises shampooing the hair with the composition as claimed in claim 6.

20. A method of dyeing human hair, which comprises shampooing the hair with the composition as claimed in claim 7.

21. A method of dyeing human hair, which comprises shampooing the hair with the composition as claimed in claim 8.

22. A method of dyeing human hair, which comprises shampooing the hair with the composition as claimed in claim 9.

23. A method of dyeing human hair, which comprises shampooing the hair with the composition as claimed in claim 10.

24. A method of dyeing human hair, which comprises shampooing the hair with the composition as claimed in claim 11.

25. A method of dyeing human hair, which comprises shampooing the hair with the composition as claimed in claim 12.

26. A method of dyeing human hair, which comprises shampooing the hair with the composition as claimed in claim 13.

27. A one-part coloring depositing shampoo composition for human hair comprising:
   at least one cationic dye, wherein said total amount, by weight, of cationic dye is 0.0005% to 3.0%;
   a non-ionic surfactant that is n-methyl alkyl glucamide with a carbon chain length greater than or equal to 8 and less than or equal to 20; and
   an aqueous carrier;
   wherein said composition does not contain any anionic surfactant.

28. The composition of claim 27, wherein said composition comprises, by weight 2.5 to 30 percent n-methyl alkyl glucamide.

* * * * *